United States Patent [19]

Lehman

[11] Patent Number: 4,815,639
[45] Date of Patent: Mar. 28, 1989

[54] INFANT CARRIER

[76] Inventor: Michael Lehman, 1133 Van Nuys St., San Diego, Calif. 92109

[21] Appl. No.: 106,046

[22] Filed: Oct. 8, 1987

[51] Int. Cl.⁴ .................................................. A61G 5/00
[52] U.S. Cl. ..................................... 224/159; 128/94; 294/140
[58] Field of Search .............................. 224/158–161, 224/202, 205, 257, 267, 907; 128/94; 294/140

[56] References Cited

U.S. PATENT DOCUMENTS

| | | | |
|---|---|---|---|
| 2,298,694 | 10/1942 | Haislip | 224/205 X |
| 2,652,050 | 9/1953 | Schoeller | 224/257 X |
| 3,215,138 | 11/1965 | Groesbeck | 128/94 |
| 4,214,579 | 7/1980 | Ford | 128/94 |
| 4,220,302 | 9/1980 | Hampton et al. | 224/205 X |
| 4,327,909 | 5/1982 | Neufeld | 128/94 X |
| 4,491,129 | 1/1985 | Lockwood | 128/94 |
| 4,553,779 | 11/1985 | Shortridge | 224/917 |
| 4,673,118 | 6/1987 | Kronz | 224/917 X |

FOREIGN PATENT DOCUMENTS 83946  7/1954  Norway ............................... 224/205

Primary Examiner—Stephen Marcus
Attorney, Agent, or Firm—Charmasson & Holz

[57] ABSTRACT

An infant carrier in the shape of a sling having a supporting strap which forms a loop passing over one of the user's shoulders, across the back diagonally, under the other shoulder and being closed over the chest. A cuff shaped and dimensioned to engage and support the user's infant carrying forearm hangs from the strap. A drooling bib attached to the strap covers the shoulder above the infant-carrying forearm. A sitting pad is also provided which can be wrapped around the infant-supporting forearm.

14 Claims, 2 Drawing Sheets

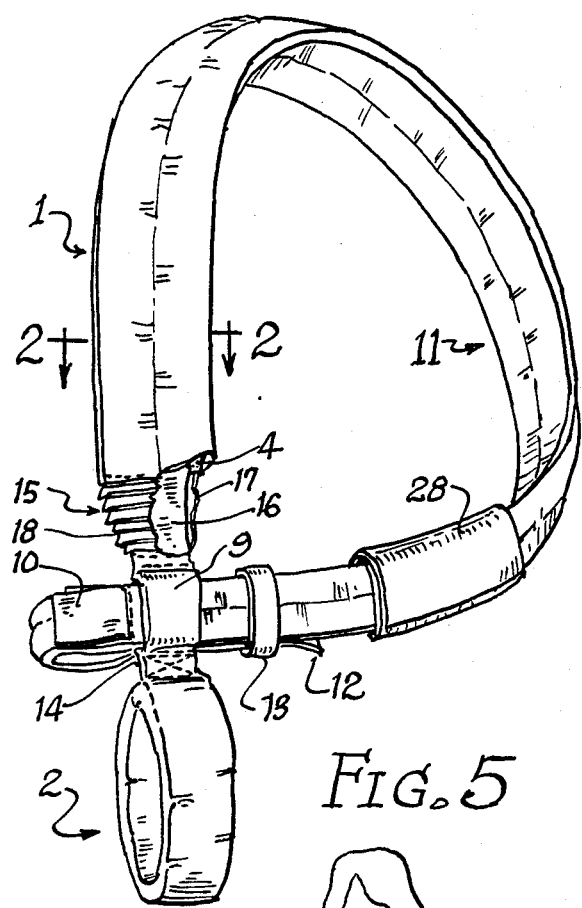
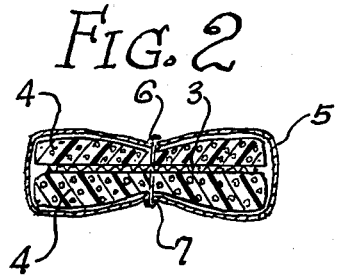
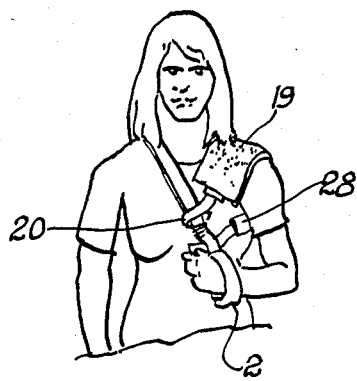
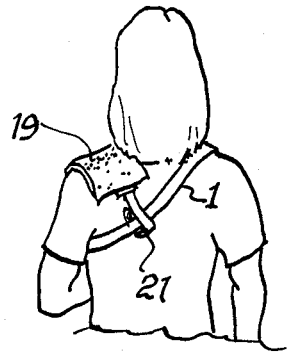
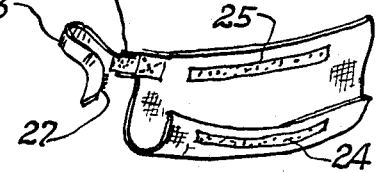

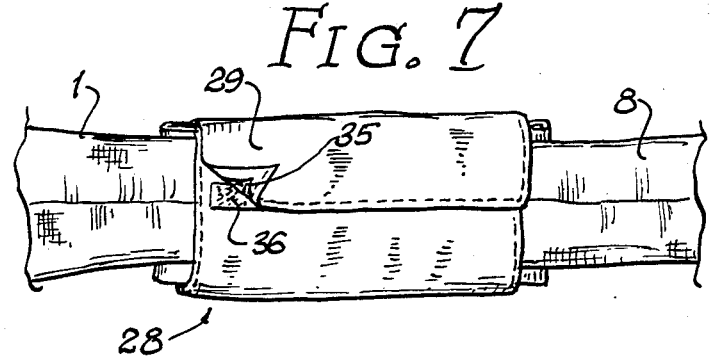
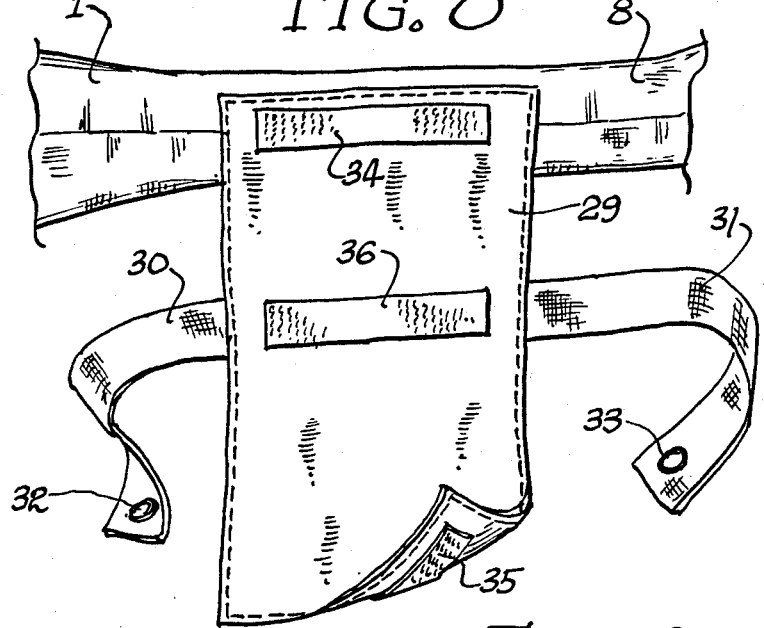
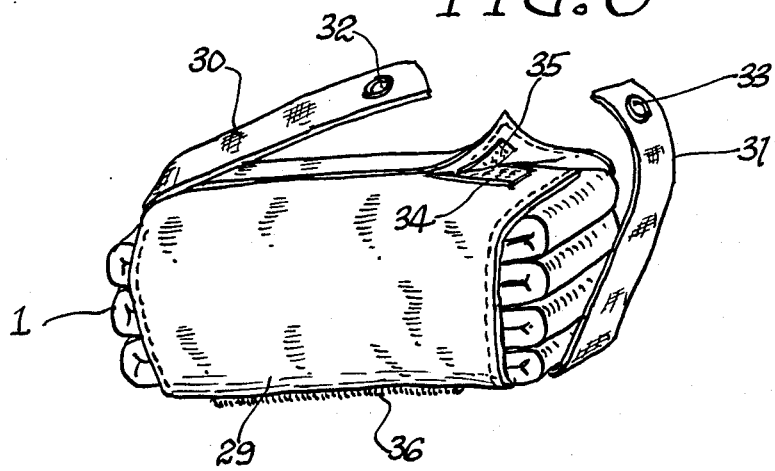

INFANT CARRIER

BACKGROUND OF THE INVENTION

This invention relates to slings and to devices used for carrying infants by direct attachments to the user's body. The only prior art known to the applicant which may be pertinent to this invention can be found in medical slings used to immobilize and support healing shoulders, arms and forearms.

Carrying a baby or infant for long periods of time over the arm can be very tiring. Infants of a certain age tend to be very active and are not content to lean against the carrying person's shoulder, therefore distributing their weight between that persons's forearm and the shoulder and chest. Instead, an active child tends to sit straight over the carriers's forearm, twist his upper body in order to look in all directions around him, and even exert pressure with his feet and legs against the carrier's waist gaining more freedom of movement. All these maneuvers contribute to the discomfort of the carrying person and limit that person's ability to carry the infant for any substantial period of time.

SUMMARY OF THE INVENTION

The main and secondary objects of the instant invention are to palliate the forementioned problems by providing a simple device which supports the infant-carrying forearm in a very comfortable and safe manner. This is accomplished by a sling including a longitudinally resilient strap which passes over one of the user's shoulders to which is attached a cuff designed to engage the wrist or the distal end of the carrying forearm.

BRIEF DESCRIPTION OF THE DRAWING

FIG. 1 is a perspective view of the sling strap and cuff;

FIG. 2 is a cross-sectional view taken along line 2—2 of FIG. 1 and showing the internal construction of the strap;

FIG. 3 is a front view of a person equipped with the carrier;

FIG. 4 is a back view thereof;

FIG. 5 is a frontal view of a person carrying an infant using the carrier;

FIG. 6 is a perspective view of the arm pad;

FIG. 7 is a back view of the carrying pouch in the folded position;

FIG. 8 is a back view of the carrying pouch in the deployed or open position; and FIG. 9 is a perspective view of the carrier folded inside the carrying pouch.

DESCRIPTION OF THE PREFERRED EMBODIMENT OF THE INVENTION

Referring now to the drawing, there is shown in FIG. 1 the basic sling structure of the carrier which consists essentially of a strap 1 and a cuff 2. As illustrated in FIG. 2, the strap 1 is made from a piece of nylon webbing 3 sandwiched between two layers of snnethetic foam. The strap is surrounded by a fabric sleeve 5 with a seam running along the center of the strap 6 and having stitches 7 which passes through the center of the web 3, the two layers of foam 4 and the two opposite sides of the fabric sleeve 5. This type of construction provides for an attractive and comfortable strap due to the cushioning effect of the foam layes 4. At one end the strap 1 tapers down to a narrower section 8 which is dimensioned to engage through a loop 9 formed at the other end of the strap 1. The narrow end section 8 is also equipped with a clampable slider 10 which can be adjustably positioned to determine the size of the closed loop 11 formed by the strap. The tip 12 of the free end of the strap is folded back on itself and secured by a ring 13 positioned on the other side of the loop 9. The cuff 2 which is formed in the same manner as the strap 1 from a cushion web, is attached below the connecting loop 9 by means of a short strap 14. Just above the connecting loop 9 the strap has a longitudinally resilient section 15 whose construction is visible through the cutout. The resilient section comprises a strip of elastic material 16 which spans a bunched-up small section 17 of the structural web 3. Folds 18 in the surrounding sleeve 5 allow that section of the strap to extend under tension until the bunched-up section of the web 17 is fully extended, but to return to its initial position under the pull of the stretched elastic element 16 when the tension is relieved.

FIGS. 3 and 4 illustrate the placement of the carrier on a person with the addition of a drooling pad 19. The user engages the head and the arm which is to support the baby through the loop 11 so that the strap passes over one shoulder, across the back then under the shoulder corresponding to the carrying arm. The wrist or forearm on which the child is to be carried is then engaged through the cuff 2. The drooling bib 19 is dimensioned to cover the shoulder of the user on the side of which the infant is to be carried. Small strap connections 20 and 21 attached at opposite ends of the bib 19 are used to secure the bib to the front and back sections of the strap 1. The strap connections are secured to those sections of the strap by any one of the well-known fastening device such as snaps, hook-and-vane fabric fasteners, buckles or rings. The pad 19 is covered with a lining of moisture absorbent material such as terry cloth or the like, and preferably in such a manner that this lining can be conveniently removed for washing without having to wash the entire carrier.

FIG. 5 illustrates the actual use of the carrier with the addition of a sitting pad 22 which wraps around the carrying forearm and attaches by means of a short connecting strap 23 to the cuff 2. FIG. 6 shows an enlarged view of the sitting pad 22 which is made preferably from a cushioning fabric which can be easily washed. Hook-and-vane fabric fasteners 24 and 25 are used to secure the pad around the forearm of the user. The same type of fasteners 26, 27 are used to secure the connecting strap 23 to the cuff 2.

The entire carrier assembly cna be conveniently folded and stored in a carrying pouch 28 which is attached to the strap 1 at the beginning of the tapering section 8 as illustrated in FIGS. 1 and 3. FIG. 8 more specifically illustrates the construction of the carrying pouch 28. The pad consists essentially of a rectangular wrap 29 provided with three interconnecting strips of hook-and-vane fasteners 34, 35 and 36, each conveniently placed to allow a multiple use of the wrap 29. When the carrier is in use, the wrap is folded twice upon itself around the tapered section 8 of the strap 1 so that the front facing fastener 35 cooperates with the middle fastener 36 to hold the wrap in a unobtrusive position which does not interfere with the use of the carrier. Actually, the position of the folded wrap just ahead of the user's armpit as better seen in FIG. 3, forms a barrier which prevents that section of the loop 11 from slipping under the user's arm. When the carrier is not in use it can be folded upon itself several times into a bundle that is then tightly circumscribed by the wrap 29 folded so that the fastener 35 at the outer edge of the wrap comes in contact with the fastener 34 at the opposite end. Two carrying straps 30 and 31 attached respectively to either side of the wrap 39 can be used to suspend the folded carrier to the user's belt or any other convenient place. The carrying straps 30 and 31 are provided with cooperating snaps 32 and 33 at their respective ends for that purpose. When the carrier is in use the carrying straps 30 and 31 are conveniently folded under the wrap 39 as shown in FIG. 7.

While the preferred embodiment of the invention has been disclosed, modifications can be made and other embodiments can be devised without departing from the spirit of the invention and the scope of the appended claims.

What is claimed is:

1. A sling for use by a person when carrying a child primarily over one forearm portion of an arm which comprises:

a flexible strap shaped and dimensioned to form a loop passing over a first one of said person's shoulder and under the second shoulder, said strap capable of supporting the weight of said child in conjunction with said person's arm;

cooperating pairs of means at both ends of said strap for adjustably closing said loop;

a flexible cuff affixed to a section of said strap, said cuff being dimensioned to receive and support portions of said arm proximate to the wrist of said forearm and provide an area on said arm for carrying said child against the body of said person; and resilient means for cushioning the pressure of said cuff against said forearm carrying said child.

2. The sling claimed in claim 1, wherein said cushioning means comprise a first resilient pad lining the inside of said cuff.

3. The sling claimed in claim 2, wherein said cushioning means comprise a second resilient pad lining said strap.

4. The sling claimed in claim 3, wherein said cushioning means comprise a longitudinally resilient section of said loop.

5. The sling claimed in claim 1 wherein said flexible cuff is shaped and dimensioned to receive and support the hand and wrist portions of said arm.

6. The sling claimed in claim 1 which further comprises a carrying pouch attached to said strap.

7. The sling claimed in claim 6, wherein said pouch comprises a wrap shaped and dimensioned to contain said strap.

8. The sling claimed in claim 7 wherein said pouch is placed on said strap proximate said person's body between said second shoulder and said cuff when worn by said person.

9. The sling claimed in claim 8 wherein said pouch is further shaped and dimensioned to form a barrier preventing said cuff from moving under said second shoulder.

10. The sling claimed in claim 9 wherein said flexible strap, means of closing, means of cushioning, and flexible cuff are foldable into said pouch and said pouch is attachable to said person.

11. A sling for use by a person when carrying a child over one forearm which comprises:

a strap shaped and dimensioned to form a loop passing over a first one of said person's shoulder and under the second shoulder;

cooperating pairs of means at both ends of said strap for adjustably closing said loop;

a cuff affixed to a section of said strap, said cuff being dimensioned to receive and support said forearm;

resilient means for cushioning the pressure of said cuff against said forearm;

a drooling bib shaped and dimensioned to cover said second shoulder; and means for removably securing said bib to said strap.

12. The sling claimed in claim 11, wherein said means for removably securing comprises:

a pair of first and second web sections, said first web section having one end permanently attached to a first side of said bib and the opposite end being removably attached to a portion of said strap going over the person's chest, and said second section having one end permanently attached to a second side of said bib opposite said first side and having its other end removably attached to a portion of said strap passing behind the person's back.

13. The sling claimed in claim 12 which further comprises a seating pad shaped and dimensioned to wrap around said forearm.

14. The sling claimed in claim 13, wherein said pad comprise means for attachment to said cuff.

* * * * *